United States Patent
Miyasaka et al.

(10) Patent No.: US 7,600,412 B2
(45) Date of Patent: Oct. 13, 2009

(54) PSEUDOSTATIC PILE LOAD TESTING METHOD

(75) Inventors: Takaaki Miyasaka, Sumida-Ku (JP); Shigeki Kondo, Sumida-Ku (JP); Fumio Kuwabara, Minamisaitama-Gun (JP)

(73) Assignee: Kabushikigaisha Jiban Shikenjo, Tokyo (JP)

( * ) Notice: Subject to any disclaimer, the term of this patent is extended or adjusted under 35 U.S.C. 154(b) by 140 days.

(21) Appl. No.: 11/355,007

(22) Filed: Feb. 16, 2006

(65) Prior Publication Data

US 2006/0191316 A1    Aug. 31, 2006

(30) Foreign Application Priority Data

Feb. 25, 2005    (JP) .............................. 2005-051046

(51) Int. Cl.
    *G01N 3/34* (2006.01)
(52) U.S. Cl. .................................... 73/11.03
(58) Field of Classification Search ................ 73/12.01, 73/12.06, 12.09, 12.13, 11.03, 11.01, 12.04
    See application file for complete search history.

(56) References Cited

U.S. PATENT DOCUMENTS

| | | | | |
|---|---|---|---|---|
| 3,535,919 A | * | 10/1970 | Budlong et al. | 73/84 |
| 4,359,890 A | * | 11/1982 | Coelus | 73/12.13 |
| 4,586,366 A | * | 5/1986 | Milberger | 73/11.03 |
| 5,325,702 A | | 7/1994 | Verstraeten | 73/12.13 |
| 6,082,173 A | * | 7/2000 | Wai | 73/12.13 |

FOREIGN PATENT DOCUMENTS

| | | | |
|---|---|---|---|
| GB | 1 446 661 | | 8/1976 |
| JP | 10219603 A | * | 8/1998 |
| JP | 2002303570 A | * | 10/2002 |
| JP | 2004324352 A | * | 11/2004 |
| JP | 2005 068707 | | 3/2005 |
| JP | 2005068802 A | * | 3/2005 |
| SU | 1059068 | | 12/1983 |
| SU | 1675505 | | 9/1991 |

* cited by examiner

*Primary Examiner*—Hezron Williams
*Assistant Examiner*—Tamiko D Bellamy
(74) *Attorney, Agent, or Firm*—Bacon & Thomas, PLLC

(57) ABSTRACT

To obtain data having high reliability required for determining bearing capacity of the pile in a short time and economically, a pseudostatic pile load testing method comprises processes that a drop height of a heavy weight (2) dropped on a pile head of a pile (1) is changed higher step by step, the heavy weight (2) is dropped from each of the heights, a time change of an acceleration of the pile head by that impact is determined by an accelerometer (4) installed at the pile head, and a displacement of the pile head is determined as an integrated value of the acceleration determined by the accelerometer (4).

1 Claim, 6 Drawing Sheets

Figure 7:
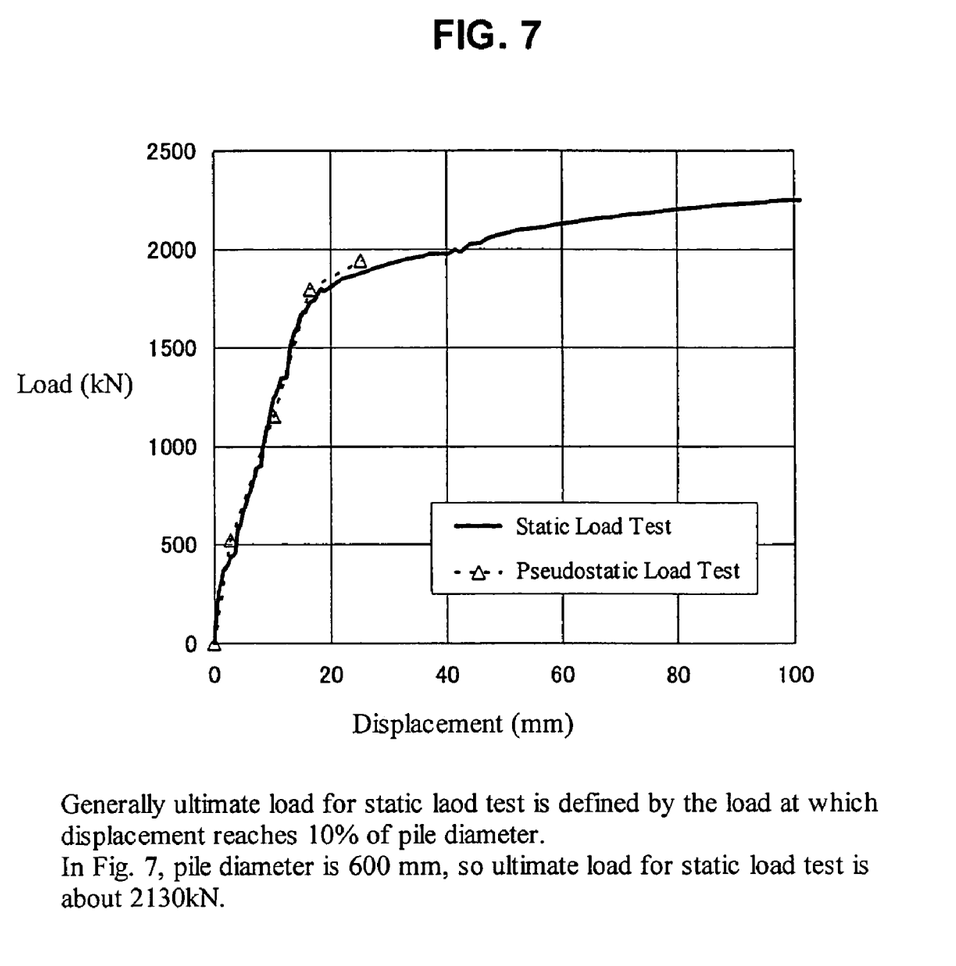
FIG. 7 is a graph showing a ground resistance-pile head settlement curve.

Generally ultimate load for static laod test is defined by the load at which displacement reaches 10% of pile diameter.
In Fig. 7, pile diameter is 600 mm, so ultimate load for static load test is about 2130kN.

PSEUDOSTATIC PILE LOAD TESTING METHOD

FIELD OF THE INVENTION

The present invention relates to a pseudostatic pile load testing method for determining bearing capacity of a pile on the basis of a relation between a load of a heavy weight and a displacement of a pile head by dropping the heavy weight on the pile head.

BACKGROUND ART

In general, a load test of a pile is executed for the purpose of obtaining a data for determining the bearing capacity, by applying a load to the pile head, and measuring a relation between the load to the pile and a displacement.

As this kind of pile load test, there have been known a static load test in which a static load is applied to a pile head step by step for a long time, and a relation between the load and a pile settlement amount is determined, and a dynamic load test, in which a heavy weight is dropped on the pile head, and a settlement amount of the pile due to an impact is measured. Further, there has been recently executed a pseudostatic load test, in which a soft cushion is put on the pile head, and the heavy load is dropped thereon.

Reference is made to a patent document, Japanese Unexamined Patent Publication No. 2002-303570, and a non-patent document, Japanese Geotechnical Society Standard, Pile Vertical Load Testing Method and Comments Thereof, Sixth Edition Pages 185 to 190 (issued by Japanese Geotechnical Society).

DISCLOSURE OF THE INVENTION

Problem to be Solved by the Invention

However, since the load is applied to the pile head for a long time, the static load test can give data having high reliability, but the static load test requires a reaction force pile, a load beam and the like so as to make the apparatus very large scale. Further, there is a problem that a lot of time is required until the necessary data is obtained.

On the contrary, in the dynamic load test, since the apparatus is simple, and the load applying time is very short such as 5 to 30 ms, it is possible to cover the shortcomings of the static load test, however, there is a problem in a reliability of the data due to the short load applying time, the impact or the like. Further, there is a problem that a cost of the apparatus is increased comparatively high, or the like.

Further, the pseudostatic load test (refer to the patent document) can give the data having a comparatively high reliability similar to the static load test in a short time, by dropping the heavy weight on the pile head via the soft cushion, thereby extending the load applying time to 30 to 200 ms corresponding to about 10 to 20 times that of the dynamic load test. However, in some weight or drop height of the heavy weight to be dropped, there is no proper cushion member which can stand against the impact load at the time of dropping the heavy weight, and there is the case that the test can not be executed.

Further, in both of the dynamic load test and the pseudostatic load test, since the settlement amount of the pile head at a time of dropping the heavy weight is measured by a measuring instrument such as a laser displacement meter or the like installed near the pile, the impact at a time of dropping the heavy weight is transmitted to the measuring instrument, and there is a risk that a reliability of the result of measurement is deteriorated.

The present invention is made for the purpose of solving the problem mentioned above, and an object of the present invention is to provide a pseudostatic pile load testing method which can give data having high reliability required for determining bearing capacity of the pile, in a short time and economically.

Effect of the Invention

In accordance with the present invention, since the displacement of the pile head caused by the load of the heavy weight dropping on the pile head is determined as an integrated value of an acceleration of the pile head at a time of dropping the heavy weight on the pile head, there can be obtained an effect that data having very high reliability can be obtained economically in a short time without requiring any particularly large-scaled apparatus and without being affected by the impact at a time of dropping the heavy weight.

Means for Solving the Problem

In accordance with a first aspect of the present invention, there is provided a pseudostatic pile load testing method for determining bearing capacity of a pile of on the basis of a relation between a load of a heavy weight and a displacement of a pile head by dropping the heavy weight on the pile head, wherein a drop height of the heavy weight is changed higher step by step, and the bearing capacity of the pile is determined on the basis of the relation between the load in each of the steps and a displacement of the pile head.

In accordance with a second aspect of the present invention, there is provided a pseudostatic pile load testing method as recited in the first aspect, wherein a cushion is put on the pile head, and the heavy weight is dropped on the cushion.

In accordance with a third aspect of the present invention, there is provided a pseudostatic pile load testing method as recited in the second aspect, wherein the cushion is formed by alternately laminating plates or blocks made of a high polymer material and metal plates.

In accordance with a fourth aspect of the present invention, there is provided a pseudostatic pile load testing method as recited in the third aspect, wherein holes in a load applying direction are formed in the plates or the blocks made of the high polymer material.

In accordance with a fifth aspect of the present invention, there is provided a pseudostatic pile load testing method as recited in the third aspect, wherein the plates or the blocks made of the high polymer material and the metal plates are adhered by dowels or an adhesive agent.

In accordance with a sixth aspect of the present invention, there is provided a pseudostatic pile load testing method as recited in the fourth aspect, wherein the plates or the blocks made of the high polymer material and the metal plates are adhered by dowels or an adhesive agent.

In accordance with a seventh aspect of the present invention, there is provided a pseudostatic pile load testing method as recited in any one of the first to sixth aspects, wherein the displacement is determined as an integrated value of an acceleration measured by an accelerometer installed at the pile head.

In accordance with an eighth aspect of the present invention, there is provided a pseudostatic pile load testing method as recited in any one of the first to sixth aspects, wherein the displacement is measured by a PSD displacement meter installed near the pile.

BRIEF DESCRIPTION OF THE DRAWINGS

FIGS. 5A, 5B and 5C show a cushion, in which

BEST MODE FOR CARRYING OUT THE INVENTION

Figure 1:
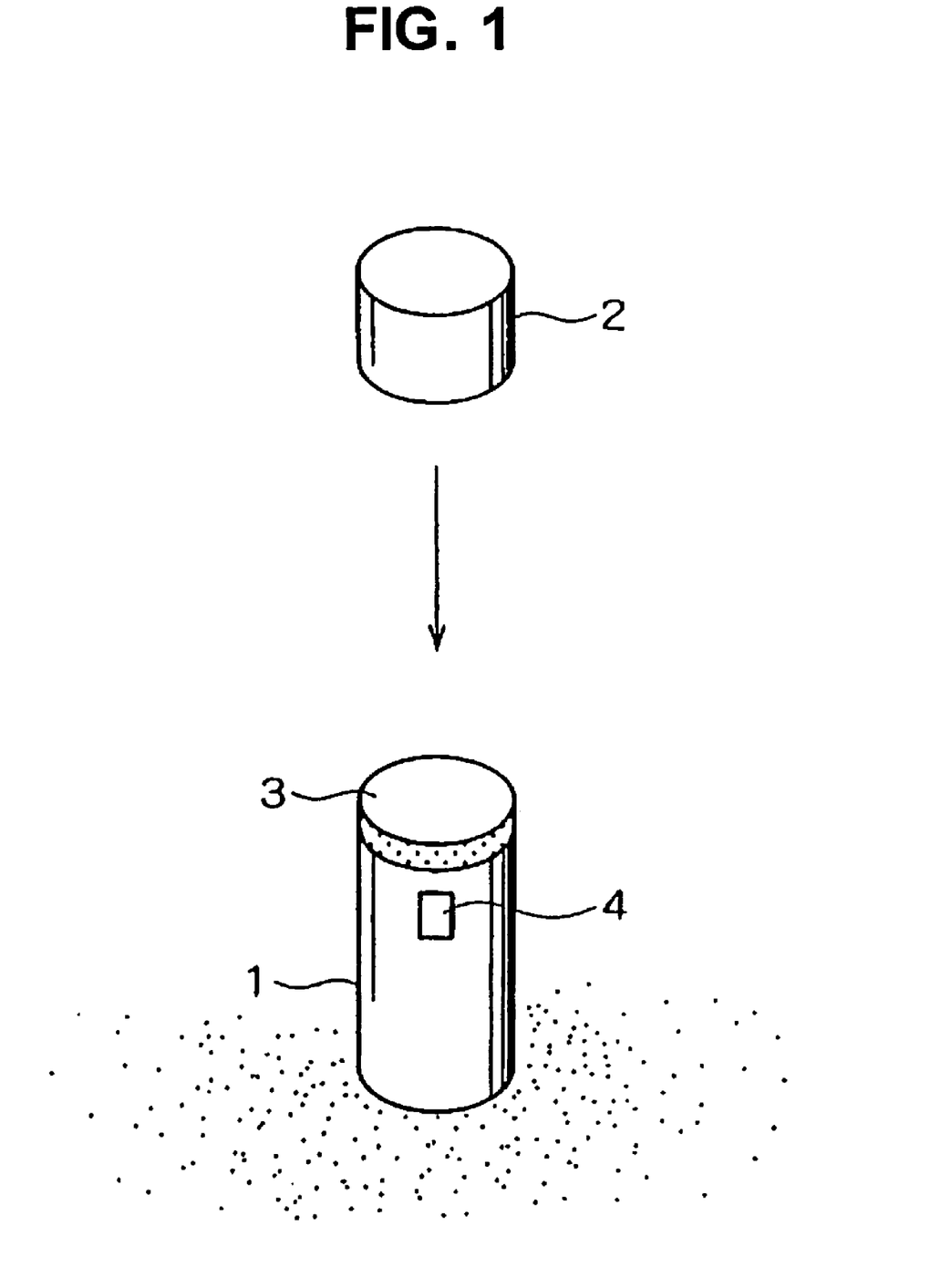
FIG. 1 is a explanatory view showing a testing method in accordance with the present invention.

FIG. 1 shows an embodiment of a pseudostatic pile load testing method in accordance with the present invention. In the drawing, reference numeral 1 denotes a pile driven in the ground for executing a load test, reference numeral 2 denotes a heavy weight dropped on a pile head of the pile 1, reference numeral 3 denotes a cushion for adjusting a load applying time, and reference numeral 4 denotes an accelerometer measuring an acceleration of the pile head at a time of dropping the heavy weight 2 on the pile head of the pile 1.

In the structure mentioned above, a description will be given of the testing method. The heavy weight 2 is dropped on the pile head of the pile 1, the acceleration of the pile head at that time is measured by the accelerometer 4 installed at the pile head, and an integrated value thereof is determined as a displacement of the pile head by the load of the heavy weight 2.

In this case, the heavy weight 2 is dropped at a plurality of times while changing the load of the heavy weight 2 (drop energy) step by step by changing a drop height of the heavy weight 2, a variation of each of the accelerations with the passage of time is measured by the accelerometer, and each of the integrated values is determined as a displacement of the pile head by each of the loads of the heavy weight 2. Then, a static load settlement characteristic of the pile 1 is estimated on the basis of the measured result, and bearing capacity of the pile 1 is determined.

Figure 3:
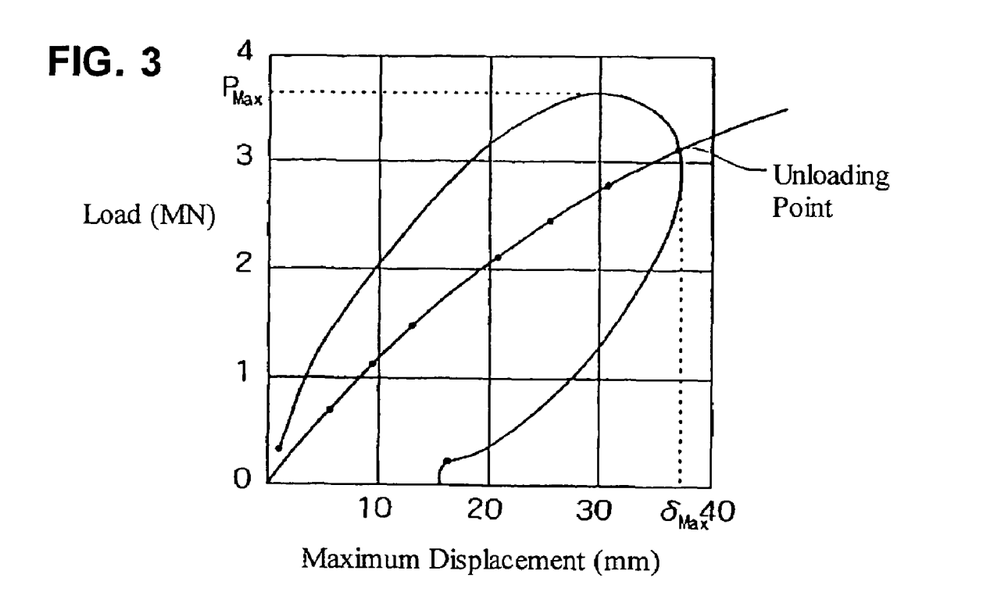
FIG. 3 is a graph showing a load-displacement curve in a pile head in accordance with a conventional pseudostatic load test.

A graph illustrated in FIG. 3 shows a load-displacement curve in the pile head in accordance with the conventional pseudostatic load test (refer to the non-patent document), and in the pseudostatic load test in which the displacement is estimated on the basis of one time pseudostatic load applying, a maximum value of the displacement tends to delay in comparison with a maximum value of the load due to a dynamic effect.

Further, bearing capacity of a pile is estimated on the basis of a theory that a ground resistance force becomes maximum at a so-called unloading point (a maximum value of the displacement), and the maximum ground resistance force is equal to the unloading point resistance force, however, there is a possibility that a great error is generated in the test result by one time pseudostatic load applying.

Figure 2:
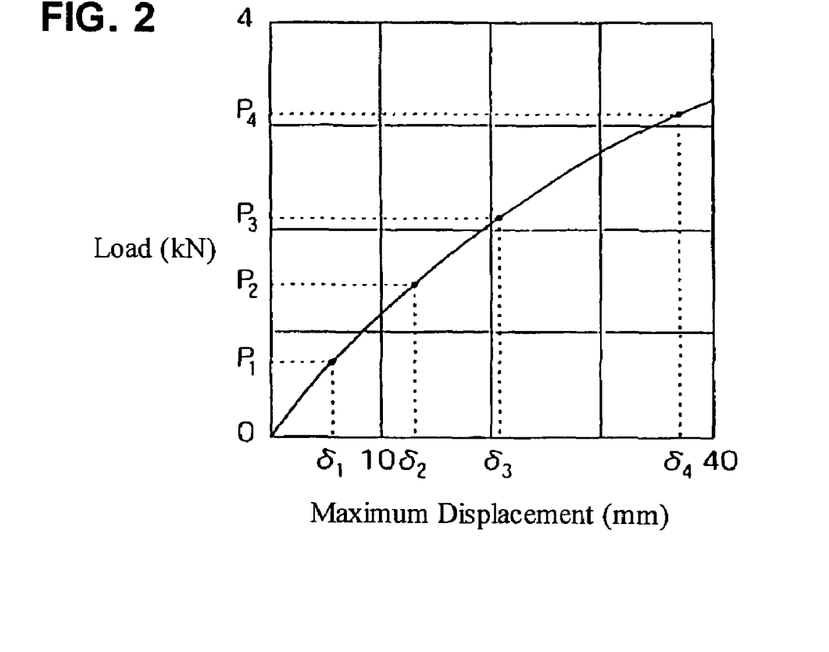
FIG. 2 is a graph showing a ground resistance settlement curve in accordance with the testing method of the present invention.

The graph illustrated in FIG. 2 shows a ground resistance settlement curve determined in accordance with the testing method of the present invention, that is, by measuring each of the accelerations at times of dropping the heavy weight 2 by the accelerometer 4, while changing the load of the heavy weight 2 (the drop energy) by changing the drop height of the heavy weight 2, and determining each of the integrated values as the displacement of the pile head generated by the load of the heavy weight 2.

As is known from the drawing, in the testing method in accordance with the present invention since some steps of measurements to an elastic behavior range or a range beyond a yield point are executed so as to make the estimation, it is possible to obtain the measurement result having a reduced error. Further, since the measurement by the accelerometer is not affected by the vibration of the ground at a time of the load applying, it is possible to execute an accurate measurement.

Figure 4:
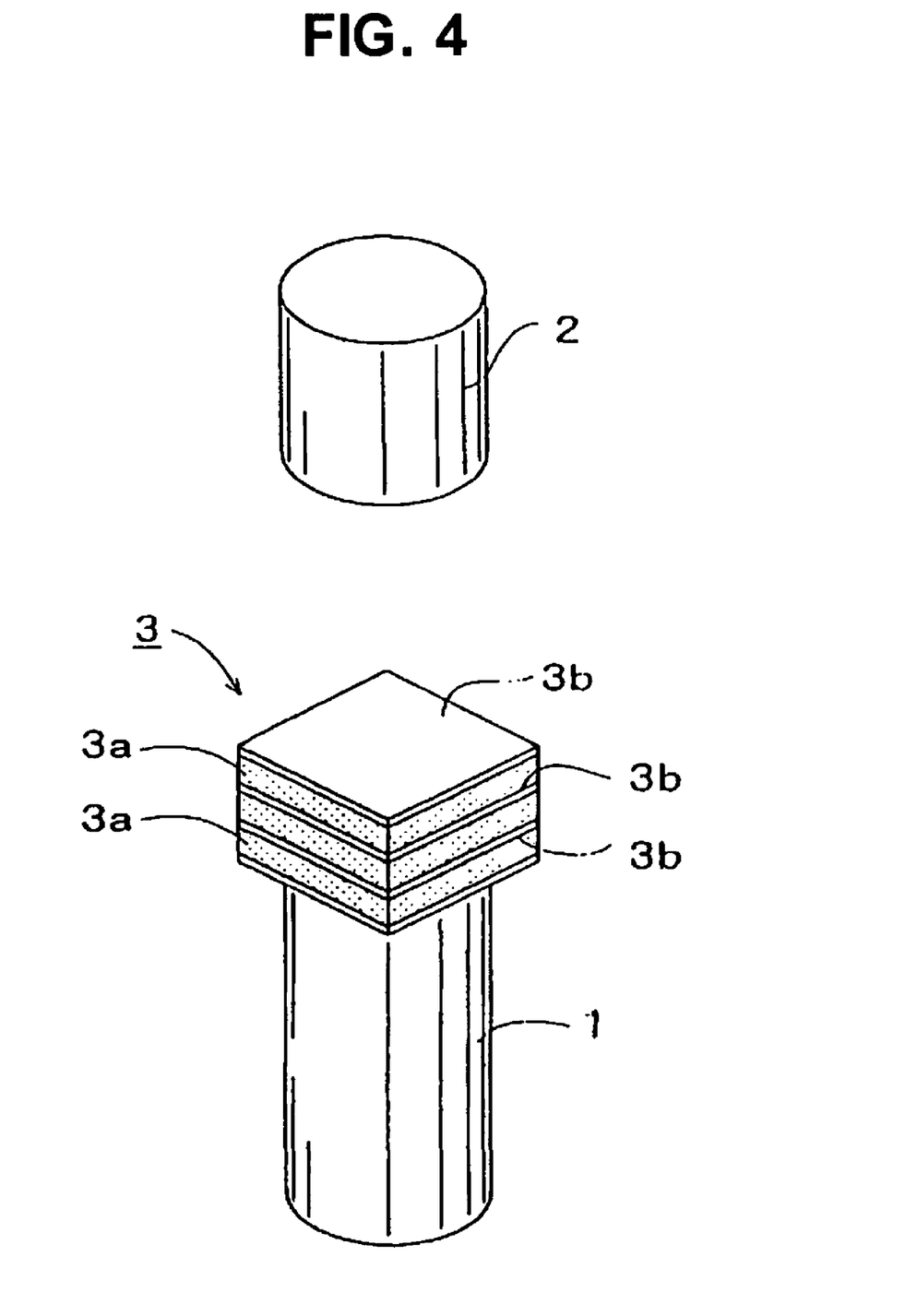
FIG. 4 is a perspective view showing the other testing method in accordance with the present invention.
Figure 5:
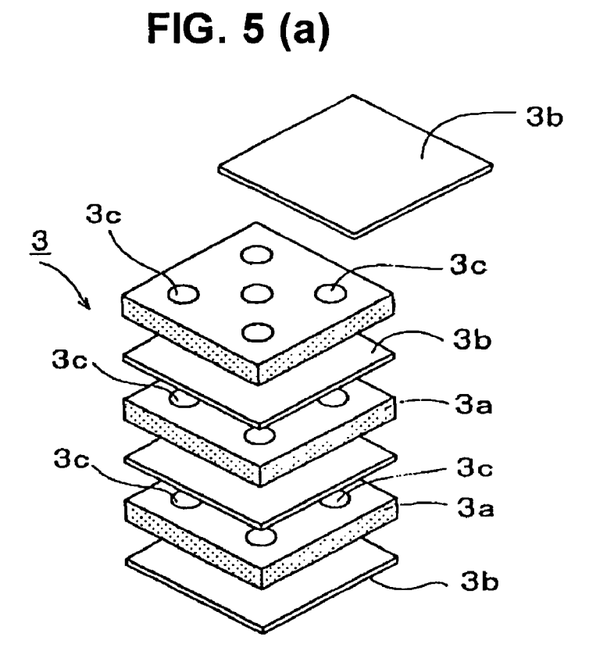
FIG. 5A is an exploded perspective view of the cushion.
FIG. 5B is a perspective view of a columnar cushion.
FIG. 5C is a vertical sectional view of the cushion.

FIGS. 4 and 5 show a modified embodiment of the cushion. The cushion 3 is formed by a plurality of plates 3a made of a high polymer material and a plurality of metal plates 3b. The plates 3a and the metal plates 3b are both formed in a rectangular plate shape, are laminated alternately, and are adhered to each other. Further, a plurality of holes 3c penetrating in a vertical direction (a load applying direction) are formed in the plate 3a.

In this case, the plate 3a may be formed by a foam resin. Further, for example, as shown in FIG. 4C, each of the plate 3a and the metal plate 3b may be adhered by dowels 3d.

The cushion 3 formed in the manner mentioned above is put on the pile head of the pile 1 driven in the ground, and an impact is applied to the pile head of the pile 1 by dropping the heavy weight 2 on the cushion 3.

In this case, since the cushion 3 is formed as a combined structure by a plurality of metal plates 3b having a very large vertical rigidity and a plurality of plates 3a (made of the high polymer material) pinched between the metal plates 3b and 3b and having a very large strain rate ($\epsilon$), it is possible to obtain data having high reliability similar to the static load test by extending the load applying time of the heavy weight 2 as much as possible while keeping the vertical rigidity equal to or more than a predetermined value, even if the heavy weight 2 is rapidly dropped on the pile head so as to apply the impact.

As the high polymer material for the plate 3a, it is possible to employ, for example, a synthetic rubber, a natural rubber, a methyl rubber or the like, and a steel plate can be employed for the metal plate 3b. Further, thicknesses, shapes and numbers thereof are not particularly limited, but can be appropriately determined.

Further, it is possible to increase the strain rate of the cushion 3 by forming a plurality of holes 3c in the plate 3a made of the high polymer material. A shape and a magnitude of the hole 3c are not particularly limited, but it is possible to adjust the strain rate of the cushion 3 by appropriately changing the shape and the magnitude of the hole 3c and increasing or reducing the number of the hole 3c. In particular, in the case that the strain rate of the high polymer material itself is large enough, the hole 3c may be omitted. Further, the hole 3c is not necessarily formed so as to penetrate.

Further, the foam resin may be used as the high polymer material, and it is possible to further increase the strain rate of the cushion 3 by forming the hole 3c penetrating in the load applying direction.

Further, it is possible to adjust the strain rate of the cushion 3 so as to adjust the load applying time of the heavy weight 2, by changing the magnitude and the shape of the hole 3c or increasing and reducing the number of the hole 3c.

In any case, it is possible to firmly fix each of the metal plates 3b to the plate 3a pinched between the metal plates 3b and 3b and made of the high polymer material by the adhesive agent, the dowels 3d or the like, and the structure may be made such that the metal plate 3b and the plate 3a made of the high polymer material are not adhered by interposing a lubricating oil between each of the metal plates 3b and the plate 3a between the metal plates 3b and 3b.

In this connection, the applicant of the present invention carries out the pseudostatic pile load test by using a large-scaled load testing apparatus with respect to the existing pile which has been cured for about three weeks after the static pressing test, and researches the ground vibration at a time of the test. In addition, the applicant carries out a wave form matching in accordance with CAPWAP, and makes a comparative study in conjunction with the pseudostatic pile load test result and the static pressing test result. The results are shown as follows.

Summary of Test

1. Test Apparatus

In order to research an influence by a mass of the heavy weight, a large-scaled heavy weight drop type test apparatus is used. The heavy weight is generally about 2% of a planed maximum load 2500 kN, however, employs a weight of 33.1 t which is about six times heavier. The load is executed in accordance with a multi cycle heavy weight drop method with a soft cushion.

2. Test Pile and Test Ground Specification

Figure 6:
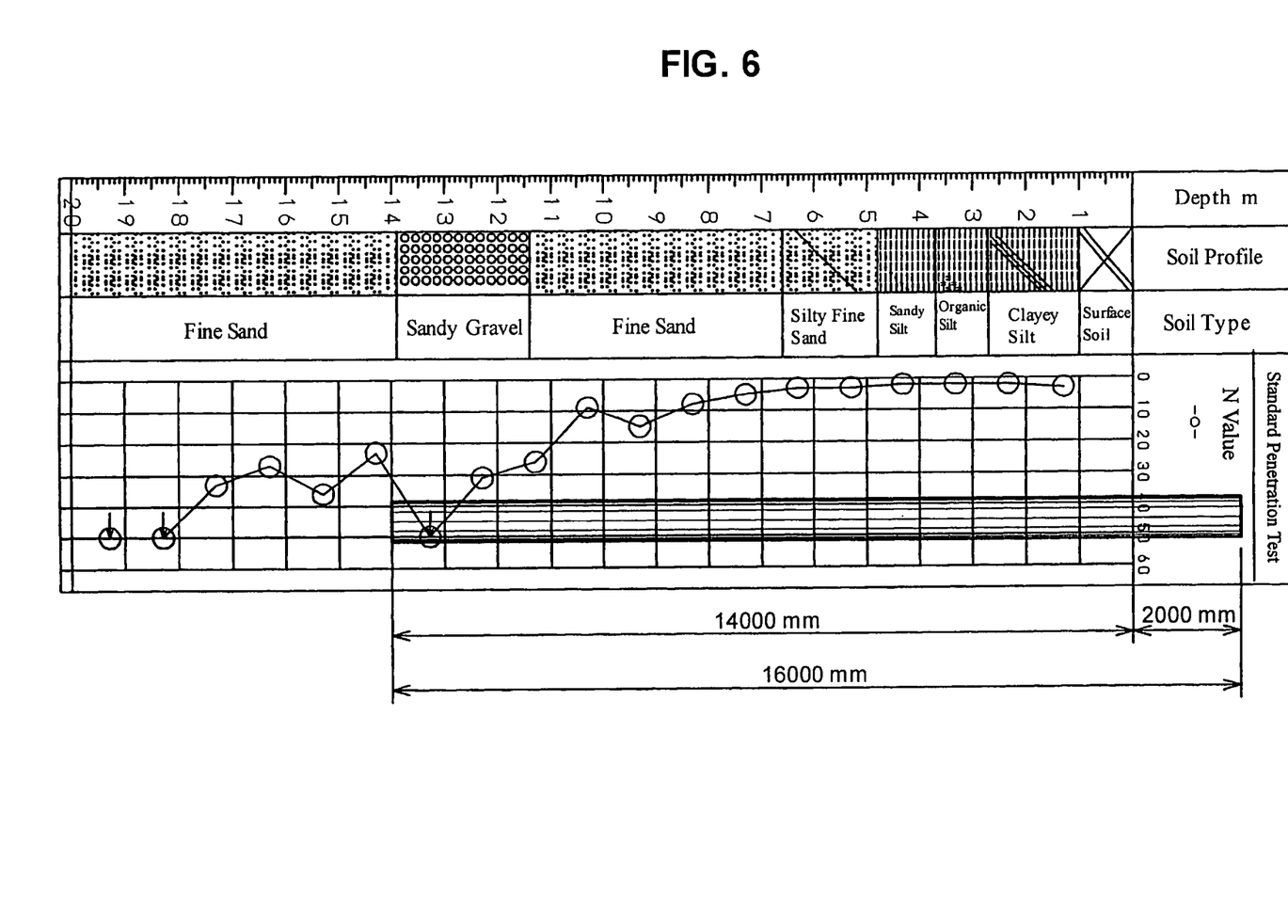
FIG. 6 is a columnar section of a test ground soil.

FIG. 6 shows a columnar section of the test ground soil. Test pile was steel tubular pile, 600 mm in diameter, driven by vibro-hammer. First, static press-in load test was conducted 1 week after pile being driven, then pseudostatic load test was conducted 3 weeks after the static press-in load test. Further, the test pile specification is as shown in Table 1.

TABLE 1

| Pile diameter Dp(mm) | Type of pile | Steel pipe thickness ts(mm) | Length L(m) | Pile mass M(t) | Installation method |
|---|---|---|---|---|---|
| 600 | Steel pipe pile | 12 | 15.9 | 3.64 | Vibro hammer driving |

A pile leading end is positioned at an upper end of a sand layer having GL-14 m and N value about 30. As the static pressing test result, as shown in Table 2, a first limit resistance is about 1780 kN, a second limit resistance is about 2130 kN, and a pile head settlement rigidity is 110 kN/mm.

TABLE 2

| First limit resistance force | | Second limit resistance force | | Pile head settlement rigidity ko(kN/mm) |
|---|---|---|---|---|
| Load(kN) | Displacement (mm) | Load(kN) | Displacement (mm) | |
| 1,780 | 18.86 | 2,126 | 60 | 110 |

3. Soft Cushion, Drop Height and Test Load

A spring constant of the soft cushion used for the test is determined, as shown in Table 3, such that it is possible to secure a time 0.062 s (in the case that the settlement rigidity of the pile is set to be infinitely great) for which the wave motion travels reciprocally about ten rounds in the pile body. Further, a relation between the planed drop height of the heavy weight of 33.1 t and the test planed load is as shown in Table 4. The planed maximum load at the maximum drop height 12 cm is about 2500 kN. The test is executed by 3 cm pitch until the maximum drop height 12 cm, and then the drop height is set to 20 cm and 50 cm in order to verify the behavior at a time of the large displacement.

TABLE 3

| Pile length L(m) | Propagation velocity V(m/s) | Travel time Round | Loading time tmin(s) | Ram mass M(kg) | Spring constant of soft cushion k(kN/m) |
|---|---|---|---|---|---|
| 15.9 | 5,120 | 10 | 0.062 | 33,100 | 86,400 |

TABLE 4

| Drop height h(cm) | Soft cushion displacement x(cm) | Planed load P(kN) |
|---|---|---|
| 3 | 1.5 | 1,280 |
| 6 | 2.1 | 1,810 |
| 9 | 2.6 | 2,220 |
| 12 | 3.0 | 2,570 |

4. Measurement Items

Measurement items are set to 4 points in a bridged type strain meter and a piezoelectric type accelerometer respectively, and 1 point in a non-contact type PSD displacement meter, as shown in Table 5.

TABLE 5

| Bridged type strain meter | 4 |
|---|---|
| Piezoelectric type accelerometer | 4 |
| Non-contact type PSD displacement meter | 1 |

5. Test Results 5-1 Pile Head Acceleration Time Change

The acceleration at a time when the pile head displacement in each of the heights becomes the maximum value is shown in Table 6 together with each of the maximum displacement values. In any drop height, it is known that the acceleration is wavy similarly to the load wave form. This seems to be caused by propagation of a stress wave. Further, referring to Table 6, it is known that the maximum acceleration until the drop height 12 cm is about 3 G, and is about 5 G in the case that the great displacement is generated. This seems to be caused by a comparatively long load applying time.

TABLE 6

| Drop height (cm) | Load Frapid(kN) | Maximum displacement S(mm) | Acceleration a(m/s$^2$) | Soil resistance Rsoil(kN) |
|---|---|---|---|---|
| 3 cm | 505 | 2.81 | −5 | 523 |
| 6 cm | 1125 | 10.30 | −8 | 1154 |
| 9 cm | 1685 | 16.56 | −30 | 1794 |
| 12 cm | 1858 | 25.12 | −23 | 1942 |

5-2 Ground Resistance-Pile Head Settlement Curve

FIG. 7 shows a ground resistance-pile head settlement curve determined by subtracting an inertia force of the pile, in combination with the static pressing test result. Viewing the pseudostatic load test result from FIG. 7, an initial pile head initial settlement rigidity is about 110 kN/mm, and approximately coincides with the static pressing test result.

Further, from the same drawing, it is known that the ground resistance yields at about 1800 kN in this test. This approximately coincides with the first limit resistance 1780 kN obtained from the static pressing test result.

Further, it is recognized that the ground resistance nature after the great displacement is generated comes to a completely different mode after 1942 kN. This seems that the nature of the pile leading end bearing ground is changed by the generation of the great displacement (the pile driving effect).

Accordingly, the maximum resistance of the original ground confirmed by this time test is about 1940 kN, and corresponds to a value which is slightly smaller than the second limit resistance (about 2130 kN at the time of the displacement 0.1 D) obtained by the static pressing test.

5-3 Wave Form Matching

The matching of the load time change graph of the drop height 12 cm is executed in accordance with the CAPWAP method. The result of the wave form matching is shown in FIG. 7 together with the pseudostatic pile load test result and the static pressing test result. It is known that the pile head displacement amount in accordance with the wave form matching becomes smallest, however, the pile head initial settlement rigidity comparatively well coincides.

6. Consideration and Summary

The maximum characteristic of this time pseudostatic pile load test is as follows.

a. The weight of the heavy weight is about 12% of the ground ultimate resistance.

b. The maximum actual load speed (at the time of H=12 cm) is about 20 MN/s in load, about 200 mm/s in settlement amount, and about 73 MPa/s with respect to the pile leading end close cross sectional area in stress intensity.

c. The actual load applying time is about 0.09 second, and corresponds to a time for which the wave motion travels reciprocally at about 14.5 rounds in the pile body.

Further, the following consideration can be obtained from this time test.

a. It is possible to confirm the stress wave propagation phenomenon.

b. It is possible to confirm the ground vibration having a frequency between 40 and 50 Hz and an amplitude about ±1 mm due to the release of the heavy weight. The ground vibration cyclic period is about 5 to 10 times shorter than the inherent cyclic period of the ground.

c. The settlement amount integrated from the acceleration indicates a greater value than the actual measurement result of the PSD displacement meter. It is considered to be possibly affected by the precision of the accelerometer or the inertia slip, and be possibly affected slightly by the vibration at the position of the PSD displacement meter.

d. The initial settlement rigidity obtained from this time test result comes to about 110 kN/mm, and well coincides with the value obtained from the static pressing test result.

e. The yield value of the original ground resistance confirmed from this time test result is about 1800 kN, and approximately coincides with the first limit resistance 1780 kN obtained from the static pressing test result.

f. The maximum resistance of the original ground confirmed from this time test result is about 1940 kN, and is slightly smaller than the second limit resistance about 2130 kN obtained from the static pressing test result.

g. The settlement amount until the yield obtained from this time test result approximately coincides with the case of the static pressing test, however, the settlement amount after the yield becomes very smaller than the case of the static pressing test.

h. The initial settlement rigidity in accordance with the wave form matching approximately coincides in comparison with the pseudostatic pile load test result and the static pressing test result.

On the basis of this time test, it is apparent that the definite initial settlement rigidity and the definite yield value of the ground resistance can be obtained by executing the multi step pseudostatic load applying.

INDUSTRIAL APPLICABILITY

It is possible to estimate a pile static load settlement characteristic having very high reliability, by executing a multi step pseudostatic load applying in accordance with the present invention.

What is claimed is:

1. A pseudostatic pile load testing method for determining bearing capacity in a yield point between a pile and a ground on the basis of a relation between a drop energy of a heavy weight and a displacement of a pile head by dropping said heavy weight through a cushion onto said pile head, said method comprising the steps of:

forming a cushion by alternately laminating plates or blocks made of a higher polymer material and metal plates, wherein holes are formed in a load applying direction in the plates or blocks;

putting said cushion on said pile head to regulate a load applying time;

attaching a displacement gage on a side of said pile head;

dropping said heavy weight onto said cushion plurality of times in succession, wherein a drop height of said heavy weight is changed from a lower position to a higher position to alter the drop energy of said heavy weight for each of successive drops, until said yield point can be obtained; and determining bearing capacity in said yield point between a pile and a ground on the basis of the relation between the drop energy and a displacement of said pile head in a last drop position of said heavy weight.

* * * * *

UNITED STATES PATENT AND TRADEMARK OFFICE
CERTIFICATE OF CORRECTION

PATENT NO. : 7,600,412 B2
APPLICATION NO. : 11/355007
DATED : October 13, 2009
INVENTOR(S) : Miyasaka et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 225 days.

Signed and Sealed this

Fifth Day of October, 2010

David J. Kappos
*Director of the United States Patent and Trademark Office*